United States Patent
Ackeret et al.

(10) Patent No.: US 6,319,253 B1
(45) Date of Patent: Nov. 20, 2001

(54) INTRAMEDULLARY NAIL WITH LOCKING HOLE

(75) Inventors: Roman Ackeret, Rheinfelden; Peter Senn, Waldenburg; Ruth Hungerbühler, Langenbruck, all of (CH)

(73) Assignee: Synthes (U.S.A), Paoli, PA (US)

( * ) Notice: Subject to any disclaimer, the term of this patent is extended or adjusted under 35 U.S.C. 154(b) by 0 days.

(21) Appl. No.: 09/654,044

(22) Filed: Sep. 1, 2000

Related U.S. Application Data

(63) Continuation of application No. PCT/CH98/00087, filed on Mar. 5, 1998.

(51) Int. Cl.⁷ ................................................... A61B 17/56
(52) U.S. Cl. ............................................. 606/64; 606/64
(58) Field of Search .............................. 606/60, 62, 64, 606/67, 68

(56) References Cited

U.S. PATENT DOCUMENTS 3,433,220  3/1969  Zickel .
4,103,683  8/1978  Neufeld .

FOREIGN PATENT DOCUMENTS 37 30 570 A1   9/1987   (DE) .
0 411 273 A1   2/1991   (EP) .
WO 98/30164    7/1998   (WO) .

*Primary Examiner*—David O. Reip
(74) *Attorney, Agent, or Firm*—Pennie & Edmonds LLP

(57) ABSTRACT

The invention relates to an intramedullary nail with a locking hole. The locking hole crosses the intramedullary nail perpendicular to the longitudinal axis of the intramedullary nail. The locking hole includes a passage which extends perpendicular to the longitudinal axis of the intramedullary nail and a borehole which does not contact the passage and also extends perpendicular to the longitudinal axis of the intramedullary nail and is displaced in the direction of the longitudinal axis in relation to the passage. The locking hole further includes a slit which connects the passage and the borehole and which in a cross-section of the intramedullary nail is not parallel to the passage.

16 Claims, 5 Drawing Sheets

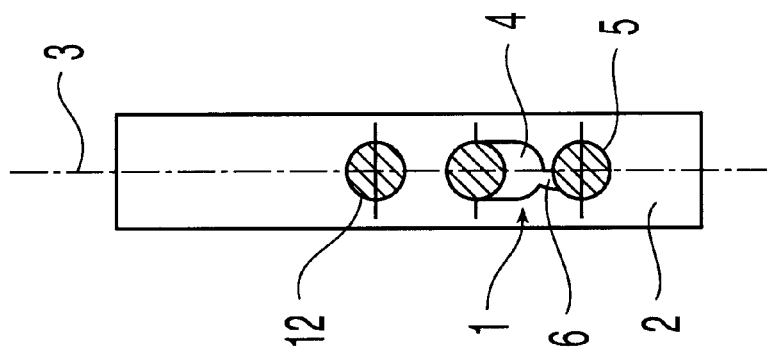
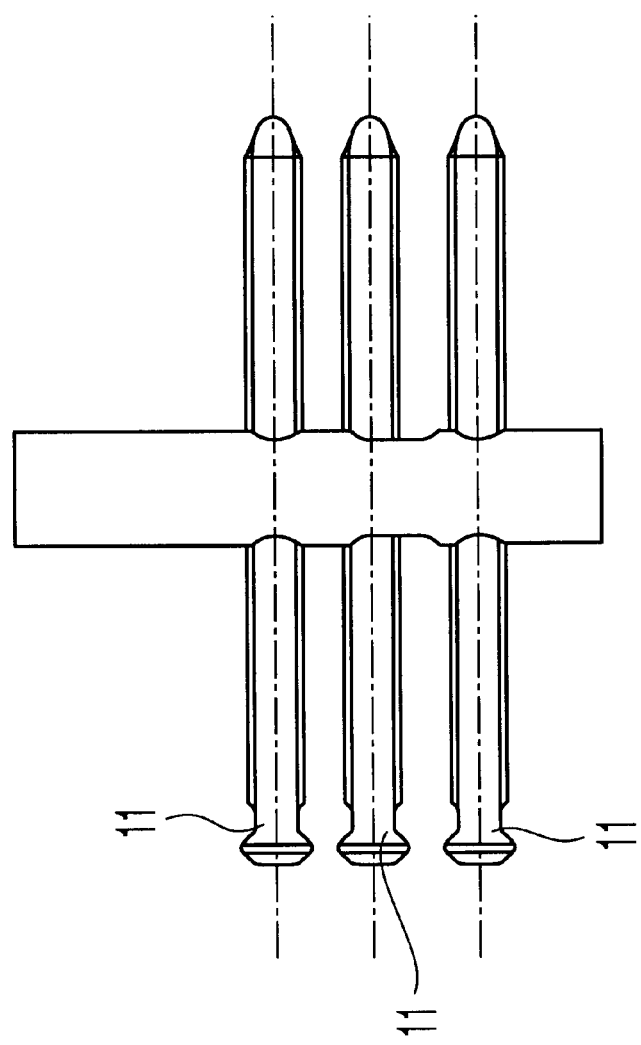
*Fig. 3a*
*Fig. 3b*

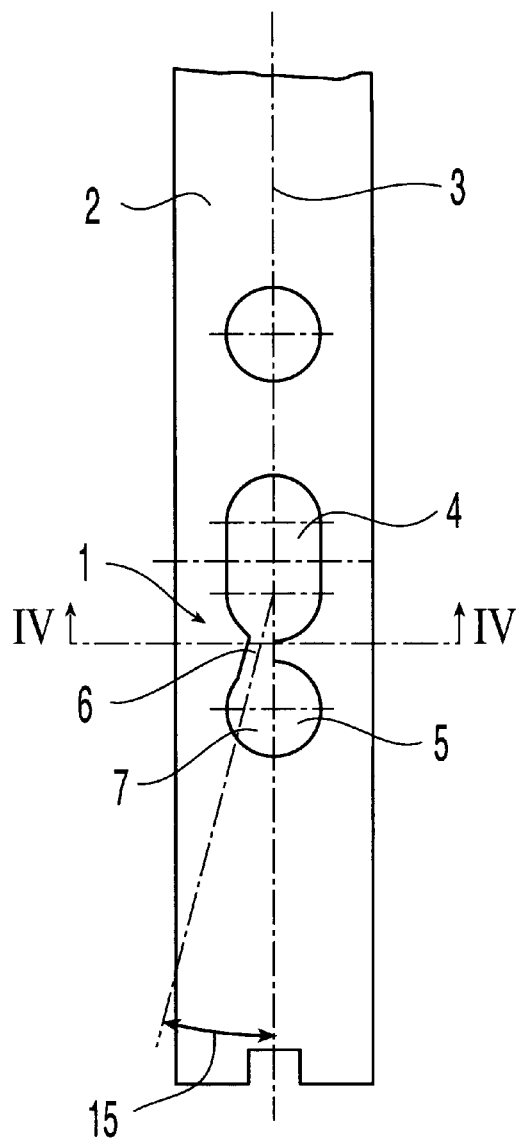
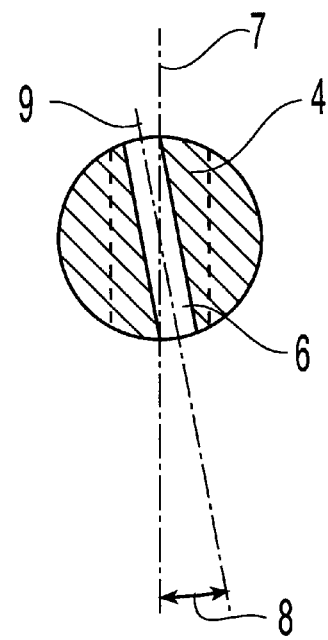
*Fig. 4a*    *Fig. 4b*

INTRAMEDULLARY NAIL WITH LOCKING HOLE

CROSS-REFERENCE TO RELATED APPLICATIONS

This application is a continuation of co-pending International Patent Application PCT/CH98/00087, filed Mar. 5, 1998, the entire content of which is expressly incorporated herein by reference thereto.

FIELD OF THE INVENTION

The present invention relates to a fracture fixation device, and in particular to a intramedullary nail.

BACKGROUND OF THE INVENTION

Intramedullary nails are frequently used for internal fixation of long bones such as the femur. These intramedullary nails are often used in conjunction with a locking element for securing the intramedullary nail within the medullary canal. One such locking element is a spiral blade inserted centrally and laterally to affix the intramedullary nail. The spiral blade is mounted in a borehole of elongated cross-section, for instance in the form of a slot or in a keyed opening of similar shape. Another locking element that can be used is locking screws which also are inserted centrally and laterally to prevent the intramedullary nail from shifting along its longitudinal direction. Because of the different geometries of the spiral blades and locking screws, current and conventional apertures receiving the locking element are configured in such a way that the intramedullary nail can only be used with locking screws or only with a spiral blade. As a result, health care facilities must maintain a large inventory of intramedullary nails—some for use with spiral blades and some for use with locking screws.

Thus, there exists a need for an improved intramedullary nail that can be used with either locking screws or a spiral blade.

SUMMARY OF THE INVENTION

The present invention relates to an intramedullary nail having a locking hole crossing the nail transversely to the longitudinal axis. The locking hole comprises an elongated passage penetrating the nail transversely to the longitudinal axis, a borehole penetrating the nail transversely to the longitudinal axis spaced from the passage along the longitudinal axis, and a slot extending through the thickness of the nail and connecting the passage and the borehole. The passage and slot are configured and dimensioned to receive a spiral blade therein with at least a portion of the blade extending into the slot. Thus, the locking hole is configured in such manner that it allows a spiral blade to be inserted in it laterally and centrally. The geometry of the locking hole is such as to also allow implanting two screws crossing the nail laterally and centrally. The intramedullary nail can also be provided with an auxiliary through hole for receiving a third locking screw.

With respect to their longitudinal axes, the locking screws and the spiral blade run parallel to a plane containing the longitudinal axis of the nail. Both the locking screws and the spiral blade pass diametrically through the intramedullary nail. If locking screws are used, one of the locking screws should run through the borehole to prevent axial shifting of the intramedullary nail. The other locking screw may be placed in the passage. If the locking screw in the passage is mounted at the passage edge away from the slot, then it will further contribute to prevent longitudinal displacement of the nail.

The passage can run parallel to the longitudinal axis of the nail. Alternatively, the passage and the borehole run perpendicularly to the longitudinal axis. The slot is configured and dimensioned to diametrically connect the passage and the borehole and can have an axis that is skewed with respect to the axis of the passage and/or the axis of the borehole. In one embodiment, the slot is defined by a sectional plane parallel to and containing the longitudinal axis and a second straight line subtending at a slot angle with the central axis of the borehole. The slot angle can be between about 5° and 25°.

In another embodiment, the passage and the borehole cross the intramedullary nail diametrically and are parallel. The passage can have a variety of shapes such as elliptical, circular, or oblong. If the passage has an oblong shape, the width can be substantially equal to the borehole diameter. Furthermore, the passage length to width ratio can be between about 1.1 to 2.5. In one embodiment, the slot has a width that is between about 10% to 90% of that of the passage.

BRIEF DESCRIPTION OF THE DRAWINGS

Preferred features of the present invention are disclosed in the accompanying drawings, wherein similar reference characters denote similar elements throughout the several views, and wherein:

FIG. 1b shows a cross-section taken through section I—I of FIG. 1a.

FIG. 2b is a side view with the intramedullary nail rotated 90° with respect to FIG. 2a.

FIG. 3a shows a side view of the portion of the intramedullary nail of FIG. 1a showing locking screws inserted into the locking hole. FIG. 3b is a side view with the intramedullary nail rotated 90° with respect to FIG. 3a.

FIG. 4a is a side view of a portion of another embodiment of the intramedullary nail according to the present invention. FIG. 4b shows a cross-section taken through section IV—IV of FIG. 4a.

FIG. 5b shows a cross-section taken through section V—V of FIG. 5a.

DETAILED DESCRIPTION OF PREFERRED EMBODIMENTS

Figure 1A:
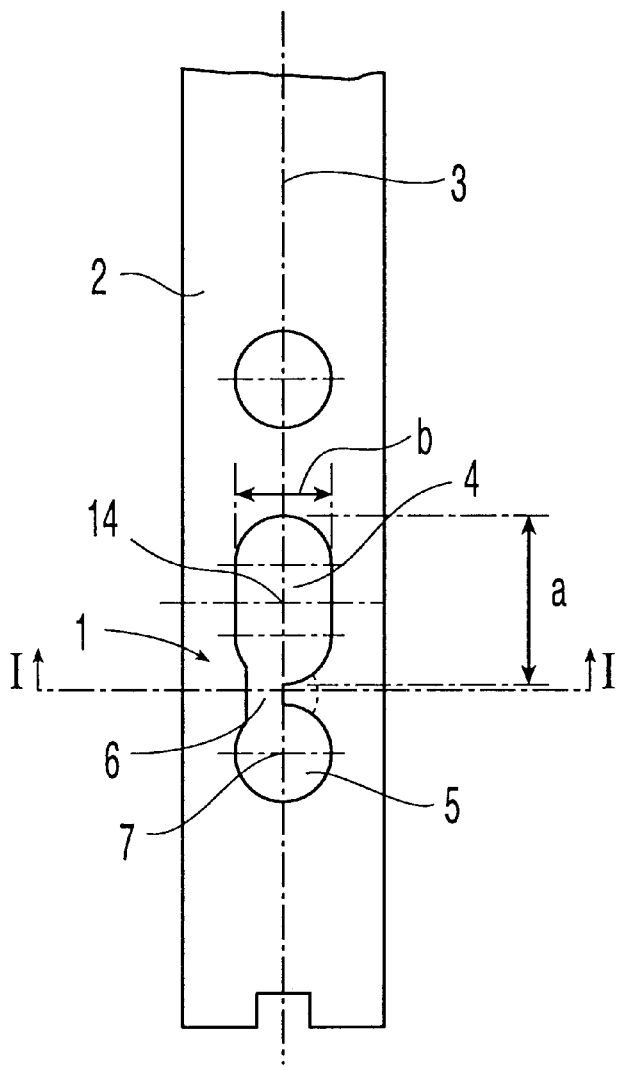
FIG. 1a is a side view of a portion of one embodiment of the intramedullary nail according to the present invention.
Figure 1B:
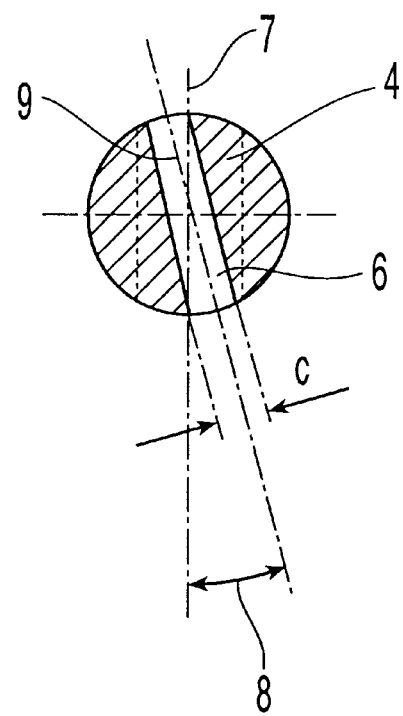

FIGS. 1a and 1b show one embodiment of the present invention. A locking hole 1 of in intramedullary nail 2 runs transversely to the longitudinal axis 3 of nail 2, which it crosses diametrically. Locking opening 1 comprises an elongated passage 4 running diametrically transversely to longitudinal axis 3 of nail 2, a borehole 5 with center axis 7 also running parallel to passage 4 and transversely to longitudinal axis 3, and a slot 6. Borehole 5 is spaced from passage 4. Slot 6 connects passage 4 and borehole 5 in the direction of longitudinal axis 3 over its entire length corresponding to the diameter of nail 2 and it crosses nail 2 transversely to longitudinal axis 3. As best seen in the cross-sectional view of FIG. 1b, slot 6 does not run parallel to passage 4, but still diametrically crosses nail 2. Slot 6 comprises a parallel sectional plane containing longitudinal axis 3 of nail 2 and a second straight line 9 subtending at an angle 8 with central axis 7 of borehole 5. In this embodiment, angle 8 is about 15°.

As shown in FIGS. 1a and b, passage 4 has an oblong shape with a length a and width b (corresponding to the diameter of borehole 5). Other geometries of passage 4 are envisioned by the present invention. For example, the cross-section of passage 4 could be oval or round.

Figure 2B:
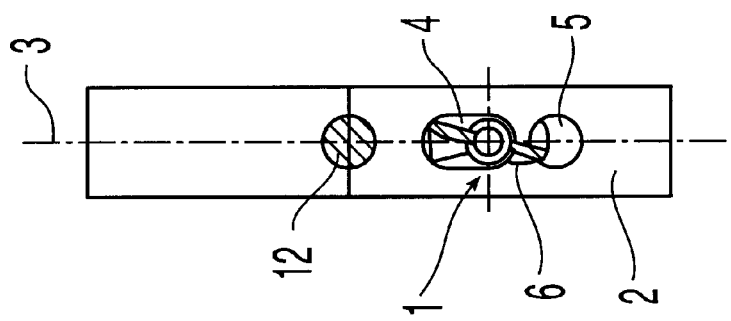
Figure 2A:
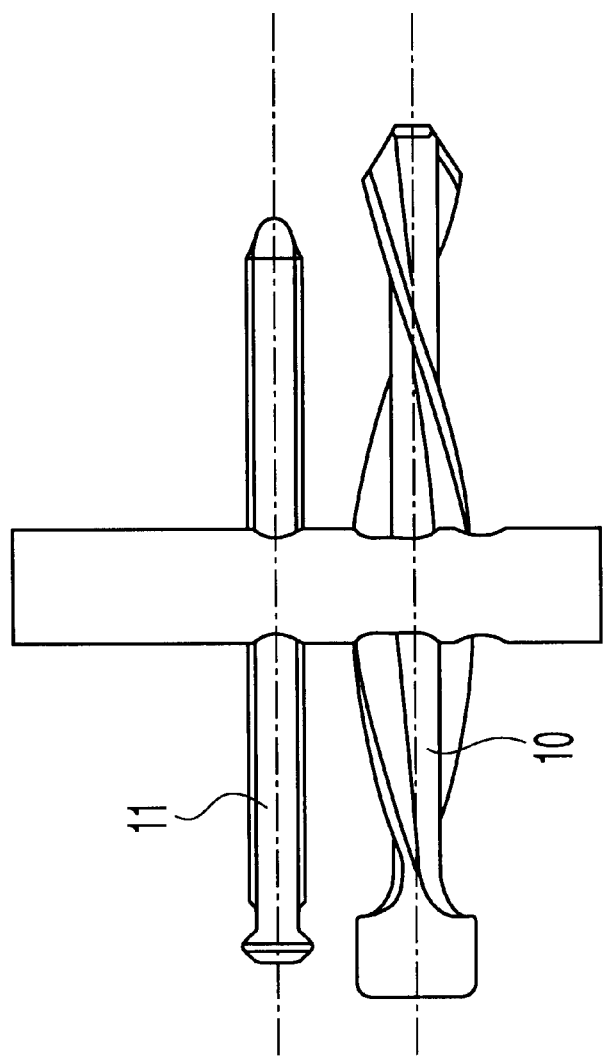
FIG. 2a is a side view of the portion of the intramedullary nail of FIG. 1a showing a spiral blade inserted into the locking hole.

FIGS. 2a and 2b show the portion of intramedullary nail 2 of FIGS. 1a and 1b with a spiral blade 10 inserted into locking hole 1. A locking screw 11 is inserted through a borehole 12 for additional fixation. FIGS. 3a and 3b show the portion of intramedullary nail of FIGS. 1a and 1b with two locking screws 11 inserted through locking hole 1 of intramedullary nail 2 and an additional locking screw 11 inserted through borehole 12. As is evident from the above description, the shape of locking hole 1 is such as to allow use of intramedullary nail 2 with either a spiral blade or several locking screws. Because of the special geometry of the locking hole, the intramedullary nail will resist movement in its longitudinal direction regardless of whether a spiral blade or locking screws are used.

FIGS. 4a and 4b show another embodiment of the present invention. Locking hole 1 differs from the embodiment shown in FIGS. 1a and 1b in that slot 6 connecting passage 4 to borehole 5 runs between the elongated slot 4 and the borehole 5 at an angle 15 relative to longitudinal axis 3 of intramedullary nail 2. As was the case for previous embodiment, slot 6 still runs diametrically and subtends at angle 8 with central axis 7 of borehole 5.

Figure 5A:
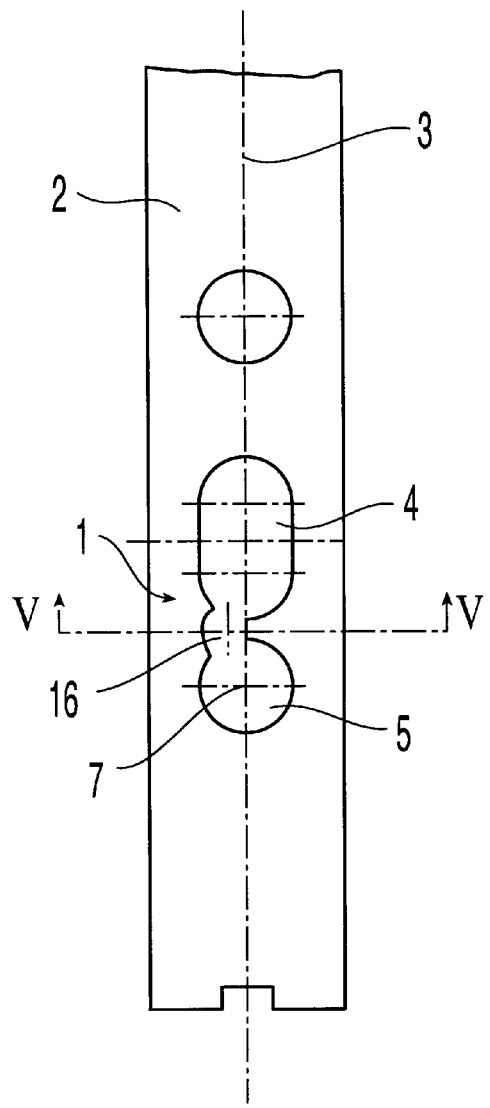
FIG. 5a is a side view of a portion of another embodiment of the intramedullary nail according to the present invention.
Figure 5B:
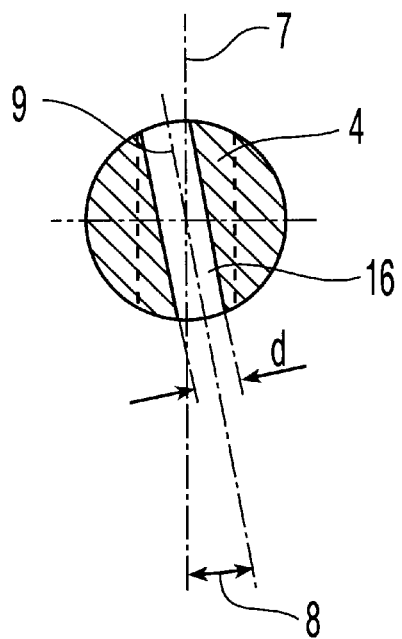

Like the above described embodiments, the embodiment shown in FIGS. 5a and 5b has locking hole 1 comprising passage 4 in the form of an elongated slot diametrically crossing intramedullary nail 2, borehole 5 with central axis 7 crossing intramedullary nail 2 diametrically and parallel to passage 4, and slot 16. Slot 16 is in the shape of a borehole of diameter d with a central axis 9 subtending at an angle 8 with central axis 7 of borehole 5.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An intramedullary nail having a thickness and a longitudinal axis, and a locking hole crossing the nail transversely to the longitudinal axis, the locking hole comprising:

an elongated passage penetrating the nail transversely to the longitudinal axis;

a borehole penetrating the nail transversely to the longitudinal axis spaced from the passage along the longitudinal axis; and a slot extending through the thickness of the nail and connecting the passage and the borehole, wherein the passage and slot are configured and dimensioned to receive a spiral blade therein with at least a portion of the blade extending into the slot.

2. The intramedullary nail of claim 1 wherein the passage has a width and a length and the length runs parallel to the longitudinal axis.

3. The intramedullary nail of claim 1 wherein the slot is configured and dimensioned to diametrically connect the passage and the borehole.

4. The intramedullary nail of claim 1 wherein the slot has an axis that is skewed with respect to the passage axis.

5. The intramedullary nail of claim 4 wherein the slot axis is skewed with respect to the borehole axis.

6. The intramedullary nail of claim 1 wherein the slot is defined by a sectional plane parallel to and containing the longitudinal axis and a second straight line subtending at a slot angle with the central axis of the borehole.

7. The intramedullary nail of claim 6 wherein the slot angle is between about 5° and 25°.

8. The intramedullary nail of claim 1 wherein the passage and the borehole cross the intramedullary nail diametrically and are parallel.

9. The intramedullary nail of claim 1 wherein the passage and the borehole run perpendicularly to the longitudinal axis.

10. The intramedullary nail of claim 1 wherein the passage has an oblong shape with a length and a width.

11. The intramedullary nail of claim 10 wherein the width is substantially equal to the borehole diameter.

12. The intramedullary nail of claim 10 wherein the slot has a width that is between about 10% to 90% of that of the passage.

13. The intramedullary nail of claim 10 wherein the passage has a length to width ratio of between about 1.1 to 2.5.

14. The intramedullary nail of claim 1 wherein the passage has a cross section that is substantially elliptic in shape.

15. The intramedullary nail of claim 1 wherein the passage has a cross section that is substantially circular in shape.

16. The intramedullary nail of claim 1 further comprising an auxiliary through hole for receiving a locking screw.

* * * * *

UNITED STATES PATENT AND TRADEMARK OFFICE
CERTIFICATE OF CORRECTION

PATENT NO.    : 6,319,253 B1
DATED         : November 20, 2001
INVENTOR(S)   : Roman Ackeret, Peter Senn, Ruth Hungerbühler and René Grass It is certified that error appears in the above-identified patent and that said Letters Patent is hereby corrected as shown below:

Title page,
Item [75] Inventors, should be corrected as shown below:

Replace: "Roman Ackeret, Rheinfelden; Peter Senn, Waldenburg; Ruth Hungerbühler, Lagenbruck, all of (CH)."
With: -- Roman Ackeret, Rheinfelden, Switzerland; Peter Senn, Waldenburg, Switzerland; Ruth Hungerbühler, Langenbruck, Switzerland; and René Grass, Dresden, Germany --.

Signed and Sealed this

Fourteenth Day of May, 2002

*Attest:*

JAMES E. ROGAN
*Attesting Officer*    *Director of the United States Patent and Trademark Office*